United States Patent [19]

Weberhofer

[11] 4,078,434

[45] Mar. 14, 1978

[54] METHOD AND APPARATUS FOR DETERMINING THE PARAMETERS OF NATURAL VIBRATION OF A SYSTEM

[75] Inventor: Josef Weberhofer, Nussbaumen, Switzerland

[73] Assignee: BBC Brown Boveri & Company Limited, Baden, Switzerland

[21] Appl. No.: 748,391

[22] Filed: Dec. 7, 1976

Related U.S. Application Data

[63] Continuation of Ser. No. 578,219, May 16, 1975, abandoned.

[30] Foreign Application Priority Data

May 20, 1974 Switzerland .......................... 6856/74

[51] Int. Cl.$^2$ ........................................... G01N 29/00
[52] U.S. Cl. .................................................... 73/593
[58] Field of Search ................... 73/67.2, 71.2, 71.4, 73/558

[56] References Cited

U.S. PATENT DOCUMENTS

| | | | |
|---|---|---|---|
| 1,994,232 | 3/1935 | Schuck | 73/558 |
| 3,070,995 | 1/1963 | Broder et al. | 73/67.2 |
| 3,089,561 | 5/1963 | Michael et al. | 73/558 |
| 3,641,550 | 2/1972 | Lynas et al. | 73/67.2 |
| 3,758,758 | 9/1973 | Games et al. | 73/67.2 |

*Primary Examiner*—Anthony V. Ciarlante
*Attorney, Agent, or Firm*—Burns, Doane, Swecker & Mathis

[57] ABSTRACT

An arrangement for ascertaining the parameters of natural vibrations and dampings of a multi-component dynamic system comprises a vibration detector applied to a component of the system for detecting and producing electrical signals constituting a measure of the mechanical vibrations produced by system internal excitement by stochastic disturbances. A frequency analyzer is connected to the signal output of the vibration detector for analyzing the signals on a progressive basis throughout the entire frequency range being examined to obtain corresponding data from which resonance curves are plotted and from which the natural frequencies and dampings of the system are obtained.

1 Claim, 3 Drawing Figures

METHOD AND APPARATUS FOR DETERMINING THE PARAMETERS OF NATURAL VIBRATION OF A SYSTEM

This is a continuation, division, of application Ser. No. 578,219 filed May 16, 1975 now abandoned.

The present invention relates to an improved method to ascertain the parameters of natural vibrations of a system, and an apparatus for the practical application of this method.

Self-excited vibrations of a system will prevent the system from operating properly, and will in many instances even endanger considerably the system, for example, in the case of self-excited shaft vibrations or rotors, or regulating systems of various types.

The ascertaining of the parameters guiding the natural vibrations of a system, that is the natural frequencies and the damping of partially rotating systems, is used primarily to determine the critical speeds and the stability limits of rotors. Several measuring techniques are known at the present time. The most important methods are:

(a) Determination of the transfer function by means of frequency-variable, periodic excitation (book by Jens Trampe Broch, Application of BRUEL & KJAER, Equipment to mechanical vibration and shock measurement, Page 28), (b) Determination of the transfer function by means of stochastic excitation (source as under a) above, Page 36), (c) Determination of the pulse response function by means of pulse excitation (source as under a) above, Page 38), (d) Determination of the cross-correlation function between stochastic excitation function and the response function of the system (BRUEL & KJAER Technical Review, 1970, Vol. 4, Page 4).

A revolving rotor is subjected in the case of the above methods to shock excitation, for example, by means of an electromagnet or by some other means, causing it to oscillate. The response function is recorded, and the natural frequencies and the dampings are thus determined.

This method has the disadvantage that special agitators are required to excite the system, especially if mechanical systems are involved. These devices are, in many instances, very complicated and costly. Very often, for example, in the case of machines in running condition, such excitation of the system will not be feasible in practice due to the size of the machine.

Since the problem is very complex, there exist still some points of doubt concerning the theory of determining the self-excited vibrations.

Simplified mechanical models for the calculation of the stability of a turbo-machine can predict trends only without being able to produce any absolute data. Usable data on the stability of the vibrations of turbine rotors can be obtained at the present time only with the aid of extensive computer programs. In this case the turbine rotor is broken down into various components, and it is necessary to enter the parameters (geometry, weight, rigidity, steam whip excitation, external damping and internal damping) for each individual component. By use of a transfer method, the computer program determines from these data the characteristic values of the entire vibrational system. Among other data, there is the need for accurate information on the characteristics of the bearings which, however, are not available with the required degree of accuracy due to boundary conditions which cannot be determined with any exactitude. Involved are the parameters: shape or bearing, clearance of bearing, type of bearing, bearing geometry, elasticity and damping properties of the bearing-lubricating oil films etc. Finally, such programs are difficult to set up and are very costly.

It is known to experts in this field, that all actual systems, and especially energy-converting systems, are excited by stochastic occurrances (for example, irregular flow of the energy carrier such as steam or electric current). These stochastic occurrences will be referred to as intrinsic disturbances.

It is a principal object of the invention to utilize the intrinsic disturbances of a system to ascertain the parameters of natural vibrations.

According to the invention the problem is solved by measuring the vibrations produced by the system as a result of internal excitement by, stochastic occurrences, and by determining by frequency analysis from the measuring signals on a progressive basis throughout the entire frequency range being examined the resonance curves, and by ascertaining therefrom the natural frequencies and the dampings of the natural vibrations of the system.

This method offers the advantage that it becomes possible to obtain in a simple manner a gauge of the potential security of the system from dynamic instability.

The reliability of system operation will be increased substantially, either by a one-time determination or by a continuous monitoring of the damping of certain natural vibrations of the system.

It is possible, by measuring the damping occurring in systems of different designs, to analyse the effects of diverse engineering details on the damping, and to establish, on the basis of the data so obtained, guide lines to be followed in new designs and developments of these critical components.

An apparatus for the practical application of this method is characterized by a vibration receiver to accept the mechanical vibrations and a frequency analyzer to process the electric vibration signal generated by the vibration receiver.

In contrast to the voluminous equipment required by the measuring systems representing the present state of the art, this newly proposed apparatus can be handled as well as transported with ease and without difficulties. Furthermore, the individual components of the apparatus are available in the market place.

The accompanying drawings depict an embodiment of the invention in a simplified form.

Figure 1:
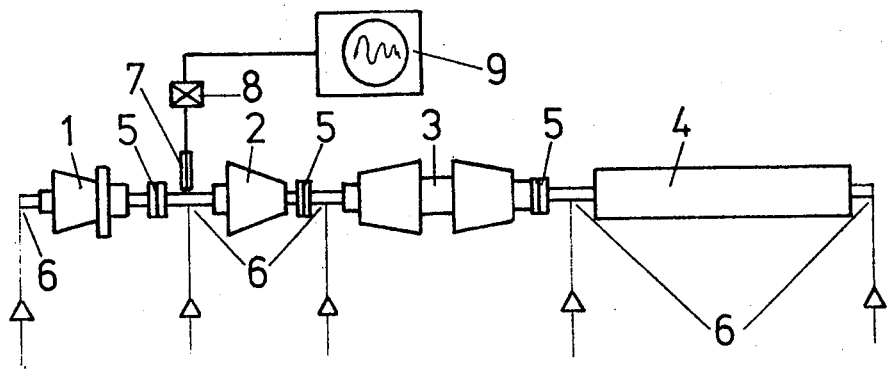
FIG. 1 shows a rotor system with five bearings and the measuring arrangement proposed by the invention in schematic form.

The rotor system shown in FIG. 1 is representative of a multi-cylinder steam turbine with generator. The blading and the various housings of the turbine are not shown. The rotor 1 of the high-pressure stage, the rotor 2 of the medium pressure stage, the double flow rotor 3 of the low-pressure stage and the electric generator 4 are coupled with each other by rigid couplings 5. This system, which in dynamic respect is to be considered as one unit, is mounted on five flexible bearings 6. The measuring and analyzing apparatus comprises one shaft-vibration-receiver 7 and one real time frequency analyzer 9.

The rotor system (1 – 5) represents, together with the bearings 6 and the, not illustrated, bearing supports, a vibration system. By exciting forces the system will be excited, while damping forces (external damping) will damp out any existing vibrations. As long as the damping forces are predominant, the system will be stable. However, when the exciting forces become predominant, the amplitude of the vibrations will increase very rapidly, in other words, the system will become unstable.

Therefore, one of the most important criteria for the avoidance of problems in rotating, especially in high-speed machines, is the protection or the damping in the bearings of such machines.

The shaft-vibration-receiver 7 is used to measure the mechanical vibrations (depending on the excitation mechanism: displacement, velocity or acceleration) at an accessible point, in the case illustrated at the bearing between rotor 1 and rotor 2. The resulting electric vibration signal is transmitted to the real time frequency analyzer 9 which is equipped with a display screen and which will ascertain the spectral density function of the shaft vibration.

It is known from the theory of the transfer functions that:
$$H_3(f) = H_2(f) \cdot H_1(f)$$

wherein:
$H_3(f)$ — spectral density function of the excited parameter (for example in the case of mechanical vibrations: displacement, velocity or acceleration)
$H_2(f)$ — transfer function of the system
$H_1(f)$ — spectral density function of the excitation parameter (for example stochastic forces)

The spectral density function of the system response therefore equals the above product.

Figure 2:
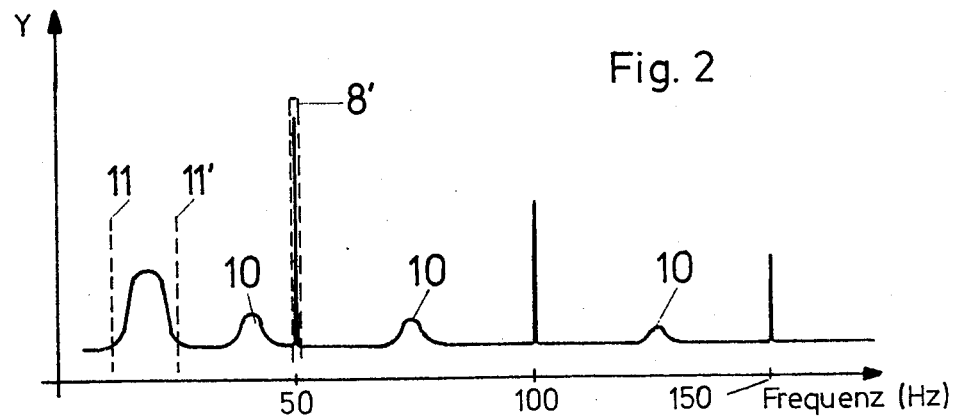
FIG. 2 shows a signal recorded by the measuring arrangement of FIG. 1, plotted in the form of a spectral density function.

If the spectral density function of the exciting parameter is flat, that is if $H_1(f) = K$, then $H_3(f) = K \cdot H_2(f)$, which means that the spectral density function of the excited parameter is proportional to the transfer function of the system. FIG. 2 depicts the spectral density function of the shaft vibration as it appears on the display screen of the real-time frequency analyzer. At the abscissa there is plotted the frequency in Hz which is analyzed on a progressive basis throughout the entire frequency range being examined, i.e. from 0 to 150+ Hz, and at the Y-axis the value Y which equals $$\frac{\text{vibration amplitude}}{\sqrt{B}},$$

where B represents the analyzer band width in Hz. The interpretation can be accomplished very easily. The periodic vibrations, excited by unbalances, show up as clear maxima with extremely steep slopes at the rotational frequency (50 Hz) and its integer multiples (100, 150 Hz). The sections at 10 and between 11 and 11', in the shape of a resonance curve, are the frequency points of the natural vibrations of the system.

The approximate location of the fundamental natural frequency is known, based on the computation of the natural frequency. In the spectral density function shown by FIG. 2 it appears in the shape of a resonance curve in the area between 11 and 11'. In practice, like in the example shown, the resonance curve of the spectral density function with the lowest frequency will also represent the resonance curve of the fundamental natural vibration.

Figure 3:
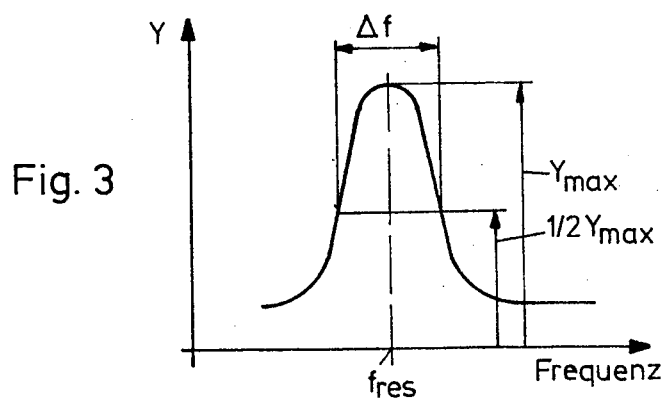
FIG. 3 shows the frequency range of interest in the form of an enlarged section of the spectral density function depicted by FIG. 2.

FIG. 3 shows the resonance curve of interest taken from the curve of FIG. 2.

The resonant frequency $f_{res}$ can be read here directly from the frequency axis, and the damping can be determined as follows:

$$D = \frac{1}{2\sqrt{3}} \cdot \frac{\Delta f}{f_{res}},$$

where
$D$ = Lehr's damping coefficient (= fraction of critical damping)
$f_{res}$ = natural frequency or resonance frequency of the system, corresponding to the maximum peak of the resonance curve
$\Delta f$ = frequency bandwidth at $\frac{1}{2} Y_{max}$ The above given equation for D holds true for $D << 1$ but is in practice sufficiently accurate up to $D < 0.3$, especially since cases with a substantially smaller damping are of primary interest. Obviously, it is also possible to determine D precisely from the shape of the resonance curve.

If the fundamental vibration appears in close proximity to the rotational frequency, it will be expedient to suppress this periodic component of the signal by means of a notch filter 8, possessing an extremely narrow notch band. The filtering effect is shown in FIG. 2 by 8', a frequency range which will not appear in the frequency spectrum.

The method, as described above, will be used to ascertain characteristic values initially or only once. If the method is to be used to monitor continuously a particularly dangerous frequency range, a frequency analyzer should be employed which operates by the principle of a tunable narrow band filter and which possesses a signal rectifier and a device for time averaging. The latter device is used to obtain representative amplitude data from the spectral components with statistically fluctuating amplitudes. The pass band (bandwidth) B of the narrow band filter must be narrow in comparison with the resonance width $B_{res}$ of the natural vibration to be analyzed; in other words $B << B_{res}$. B will govern the frequency resolution of the analysis.

Obviously, the frequency analyzer can also comprise a set of several, permanently tuned, parallel narrow-band filters, each equipped with a signal rectifier and a device for averaging in time. Here again will the bandwidth B of the individual filters govern the frequency resolution of the analysis.

In the case of the example described above, spectral density function was ascertained by means of a real time frequency analyzer. It is also possible, as an alternative, to determine the power density function or, by means of a correlator, the auto-correlation function of the vibration signals, and to ascertain the characteristic values therefrom.

Obviously, the method described above is not limited to partially rotating systems, and the method proposed by the invention, and a corresponding apparatus for its practical application can be used to ascertain in general the natural vibrations of any stochastically excited systems.

I claim:

1. The method of ascertaining the parameters of natural vibrations and dampings of a multi-component dynamic system which comprises the steps of producing signals which constitute a measure of the vibrations produced by system internal excitement by stochastic disturbances, suppressing periodic components of the vibration signals, deriving corresponding resonance curves by frequency analysis of the vibration signals on a progressive basis throughout the entire frequency range being examined and ascertaining from the resonance curves the natural frequencies and dampings of the system's natural vibrations.

* * * * *